United States Patent [19]
Scharf

[11] Patent Number: 5,830,137
[45] Date of Patent: Nov. 3, 1998

[54] GREEN LIGHT PULSE OXIMETER

[75] Inventor: John Edward Scharf, Oldsmar, Fla.

[73] Assignee: University of South Florida, Tampa, Fla.

[21] Appl. No.: 749,898

[22] Filed: Nov. 18, 1996

[51] Int. Cl.$^6$ .................................................. A61B 5/00
[52] U.S. Cl. ......................................................... 600/323
[58] Field of Search .................................... 600/310, 322, 600/323, 324, 326, 330, 476; 356/41

[56] References Cited

U.S. PATENT DOCUMENTS

| | | |
|---|---|---|
| 3,802,776 | 4/1974 | Tchang . |
| 3,815,583 | 6/1974 | Scheidt . |
| 4,109,643 | 8/1978 | Bond et al. . |

(List continued on next page.)

FOREIGN PATENT DOCUMENTS

| | | |
|---|---|---|
| 63-311937 | 12/1988 | Japan . |
| 1377605 | 2/1986 | U.S.S.R. . |
| 92/07505 | 1/1990 | WIPO . |

OTHER PUBLICATIONS

"Optimization of Portable Pulse Oximetry Through Fourier Analysis," John E. Scharf et al., IEEE, Jun. 1993, pp. 233–235, first available on Apr. 2, 1993, at the IEEE, 12th Southern Biomedical Conference at Tulane University, New Orleans, LA, held Apr. 2–4, 1993.

"Pulse Oximetry Through Spectral Analysis," John E, Scharf et al., 1993 IEEE, Jun. 1993, pp. 227–229, first available on Apr. 2, 1993, at the IEEE, 12th Southern Biomedical Conference at Tulane University, New Orleans, LA, held Apr. 2–4, 1993.

"Direct Digital Capture of Pulse Oximetry Waveforms," John E. Scharf et al., 1993 IEEE, Jun. 1993, pp. 230–232, first available on Apr. 2, 1993, at the IEEE, 12th Southern Biomedical Conference at Tulane University, New Orleans, LA, held Apr. 2–4, 1993.

Light–To–Frequency Converter—TSL220, Texas Instruments Inc., D3619, Aug. 1990, Rev. Jun. 1991.

Programmable Light–To–Frequency Converter—TSL230, Texas Instruments Inc., SOES007A, Dec. 1992, Rev. Dec. 1993.

CMOS—8–Bit Buffered Multiplying DAC—AD7524, Digital–to–Analog Converters, Rev. A, pp. 2–399, 402–403.

Burr–Brown ACF2101 Advertisement and Product Data Sheet (PDS–1079, Mar. 1991).

"In Vivo Reflectance of Blood and Tissue as a Function of Light Wavelength", Cui, et al., IEEE Transactions on Biomedical Engineering, vol. 37, No. 6, pp. 632–639, Jun. 1990.

*Primary Examiner*—Robert L. Nasser
*Assistant Examiner*—Eric F. Winakur
*Attorney, Agent, or Firm*—Sean T. Moorhead; Calfee, Halter & Griswold LLP

[57] ABSTRACT

A reflectance pulse oximeter that determines oxygen saturation of hemoglobin using two sources of electromagnetic radiation in the green optical region, which provides the maximum reflectance pulsation spectrum. The use of green light allows placement of an oximetry probe at central body sites (e.g., wrist, thigh, abdomen, forehead, scalp, and back). Preferably, the two green light sources alternately emit light at 560 nm and 577 nm, respectively, which gives the biggest difference in hemoglobin extinction coefficients between deoxyhemoglobin, RHb, and oxyhemoglobin, $HbO_2$.

41 Claims, 7 Drawing Sheets

U.S. PATENT DOCUMENTS

| | | |
|---|---|---|
| 4,167,331 | 9/1979 | Nielsen . |
| 4,266,554 | 5/1981 | Hamaguri . |
| 4,267,844 | 5/1981 | Yamanishi . |
| 4,357,105 | 11/1982 | Loretz . |
| 4,407,290 | 10/1983 | Wilber . |
| 4,447,150 | 5/1984 | Heinemann . |
| 4,498,020 | 2/1985 | Gloima et al. . |
| 4,586,513 | 5/1986 | Hamaguri . |
| 4,694,833 | 9/1987 | Hamaguri . |
| 4,800,495 | 1/1989 | Smith . |
| 4,807,630 | 2/1989 | Malinouskas . |
| 4,807,631 | 2/1989 | Hersh et al. . |
| 4,824,242 | 4/1989 | Frick et al. . |
| 4,869,254 | 9/1989 | Stone et al. . |
| 4,883,353 | 11/1989 | Hausman et al. . |
| 4,911,167 | 3/1990 | Corenman et al. . |
| 4,934,372 | 6/1990 | Corenman et al. . |
| 4,997,769 | 3/1991 | Lundsgaard . |
| 5,040,539 | 8/1991 | Schmitt et al. . |
| 5,047,208 | 9/1991 | Schweitzer et al. . |
| 5,078,136 | 1/1992 | Stone et al. . |
| 5,111,817 | 5/1992 | Clark et al. . |
| 5,113,861 | 5/1992 | Rother . |
| 5,149,503 | 9/1992 | Kohno et al. . |
| 5,167,230 | 12/1992 | Chance . |
| 5,190,038 | 3/1993 | Polson . |
| 5,299,570 | 4/1994 | Hatschek . |
| 5,308,919 | 5/1994 | Minnich . |
| 5,365,924 | 11/1994 | Erdman . |
| 5,512,940 | 4/1996 | Takasugi et al. .......... 348/71 |
| 5,524,617 | 6/1996 | Mannheimer . |
| 5,575,284 | 11/1996 | Athan et al. . |

GREEN LIGHT PULSE OXIMETER

FIELD OF THE INVENTION

The present invention relates generally to medical diagnostic instruments and, more specifically, to a pulse oximeter using two green light sources to detect the oxygen saturation of hemoglobin in a volume of intravascular blood.

BACKGROUND OF THE INVENTION

The degree of oxygen saturation of hemoglobin, $SpO_2$, in arterial blood is often a vital index of the condition of a patient. As blood is pulsed through the lungs by the heart action, a certain percentage of the deoxyhemoglobin, RHb, picks up oxygen so as to become oxyhemoglobin, $HbO_2$. From the lungs, the blood passes through the arterial system until it reaches the capillaries at which point a portion of the $HbO_2$ gives up its oxygen to support the life processes in adjacent cells.

By medical definition, the oxygen saturation level is the percentage of $HbO_2$ divided by the total hemoglobin; therefore, $SpO_2 = HbO_2/(RHb+HbO_2)$. The saturation value is a very important physiological value. A healthy, conscious person will have an oxygen saturation of approximately 96 to 98%. A person can lose consciousness or suffer permanent brain damage if that person's oxygen saturation value falls to very low levels for extended periods of time. Because of the importance of the oxygen saturation value, "Pulse oximetry has been recommended as a standard of care for every general anesthetic." Kevin K. Tremper & Steven J. Barker, *Pulse Oximetry*, Anesthesiology, January 1989, at 98.

An oximeter determines the saturation value by analyzing the change in color of the blood. When radiant energy interacts with a liquid, certain wavelengths may be selectively absorbed by particles which are dissolved therein. For a given path length that the light traverses through the liquid, Beer's law (the Beer-Lambert or Bouguer-Beer relation) indicates that the relative reduction in radiation power (P/Po) at a given wavelength is an inverse logarithmic function of the concentration of the solute in the liquid that absorbs that wavelength.

For a solution of oxygenated human hemoglobin, the extinction coefficient maximum is at a wavelength of about 577 nm (green). O. W. Van Assendelft, *Spectrophotometry of Haemoglobin Derivatives*, Charles C. Thomas, Publisher, 1970, Royal Vangorcum LTD., Publisher, Assen, The Netherlands. Instruments that measure this wavelength are capable of delivering clinically useful information as to oxyhemoglobin levels. In addition, the reflectance pulsation spectrum shows a peak at 577 nm as well. Weijia Cui, Lee L. Ostrander, Bok Y. Lee, "In Vivo Reflectance of Blood and Tissue as a Function of Light Wavelength", IEEE Trans. Biom. Eng. 37:6:1990, 632–639.

In general, methods for noninvasively measuring oxygen saturation in arterial blood utilize the relative difference between the electromagnetic radiation absorption coefficient of deoxyhemoglobin, RHb, and that of oxyhemoglobin, $HbO_2$. The electromagnetic radiation absorption coefficients of RHb and $HbO_2$ are characteristically tied to the wavelength of the electromagnetic radiation traveling through them.

In practice of the transmittance pulse oximetry technique, the oxygen saturation of hemoglobin in intravascular blood is determined by (1) alternatively illuminating a volume of intravascular blood with electromagnetic radiation of two or more selected wavelengths, e.g., a red (600–700 nm) wavelength and an infrared (800–940 nm) wavelength, (2) detecting the time-varying electromagnetic radiation intensity transmitted through by the intravascular blood for each of the wavelengths, and (3) calculating oxygen saturation values for the patient's blood by applying the Lambert-Beer's transmittance law to the transmitted electromagnetic radiation intensities at the selected wavelengths.

Whereas apparatus is available for making accurate measurements on a sample of blood in a cuvette, it is not always possible or desirable to withdraw blood from a patient, and it obviously impracticable to do so when continuous monitoring is required, such as while the patient is in surgery. Therefore, much effort has been expanded in devising an instrument for making the measurement by noninvasive means.

A critical limitation in prior art noninvasive pulse oximeters is the few number of acceptable sites where a pulse oximeter probe may be placed. Transmittance probes must be placed in an area of the body thin enough to pass the red/infrared frequencies of light from one side of the body part to the other, e.g., ear lobe, finger nail bed, and toe nail bed. Although red/infrared reflectance oximetry probes are known to those skilled in the art, they do not function well because red and infrared wavelengths transmit through the tissue rather than reflect back to the sensor. Therefore, red/infrared reflectance sensor probes are not typically used for many potentially important clinical applications including: use at central body sites (e.g., thigh, abdomen, and back), enhancing poor signals during hypoperfusion, decreasing motion artifact, etc.

SUMMARY OF THE INVENTION

According to the present invention, a reflectance oximeter is provided using two green light sources to detect the oxygen saturation of hemoglobin in a volume of intravascular blood. Preferably the two light sources emit green light centered at 560 nm and 577 nm, respectively, which gives the biggest difference in absorption between deoxyhemoglobin, RHb, and oxyhemoglobin, $HbO_2$. The green reflectance oximeter is a significant improvement compared to the red/infrared state of the art because the reflectance pulsation spectrum peaks at 577 nm. Practically, several combinations of two green light sources can be used. Ideally, these light sources comprise very narrow band (e.g., 1.0 nm wide) sources such as laser diodes at the desired frequencies. However, the benefits of the present invention can be realized using other green light sources, such as narrow band (e.g., 10 nm wide) light emitting diodes (LEDs) at two green frequencies (e.g., 562 nm and 574 nm) with optional ultra-narrowband (e.g., 0.5–4.0 nm wide) filters at two green frequencies (e.g., 560 nm and 577 nm).

In one embodiment of the present invention, two filtered green LEDs alternatively illuminate an intravascular blood sample with two green wavelengths of electromagnetic radiation. The electromagnetic radiation interacts with the blood and a residual optical signal is reflected by the blood. Preferably a photodiode in a light-to-frequency converter (LFC) detects the oximetry optical signals from the intravascular blood sample illuminated by the two LEDs. The LFC produces a periodic electrical signal in the form of a pulse train having a frequency proportional to the light intensity. The data becomes an input to a high-speed digital counter, either discrete or internal to a processor (e.g., digital signal processor, microprocessor, or microcontroller), which converts the pulsatile signal into a digital word suitable to be analyzed by the processor. In the alternative, a separate silicon photodiode, a current-to-voltage converter (a transimpedance amplifier), a preamplifier, a filter, a sample and hold, and an analog-to-digital (A/D) converter can be used to capture the oximetry signal.

Once inside the processor, the time-domain data is converted into the frequency domain by, for example, performing the well-known Fast Fourier Transform (FFT). The frequency domain data is then processed to determine the oxygen saturation value using any of a number of methods known to those skilled in the art.

It is therefore an advantage of the present invention to provide a green-light reflectance-type pulse oximeter capable of measuring oxygen saturation at central body surfaces.

It is a further object of this invention to provide a reflectance-type pulse oximeter using only green wavelengths of light to measure oxygen saturation.

These and other advantages of the present invention shall become more apparent from a detailed description of the invention.

BRIEF DESCRIPTION OF THE DRAWINGS

In the accompanying drawings, which are incorporated in and constitute a part of this specification, embodiments of the invention are illustrated, which, together with a general description of the invention given above, and the detailed description given below serve to example the principles of this invention.

DETAILED DESCRIPTION OF THE PREFERRED EMBODIMENT

While the present invention will be described more fully hereinafter with reference to the accompanying drawings, in which a preferred embodiment of the present invention is shown, it is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate arts, and not as limiting upon the present invention.

According to the present invention, two green light sources alternatively illuminate a patient's skin 2 and an associated intravascular blood sample 4 with two different green wavelengths of electromagnetic radiation. The electromagnetic radiation interacts with the blood 4 and a residual optical signal is reflected by the blood 4 to the LFC. A processor analyzes this optical signal, determines the oxygen saturation from the signal, and displays a number corresponding to the determined saturation value.

Figure 1:
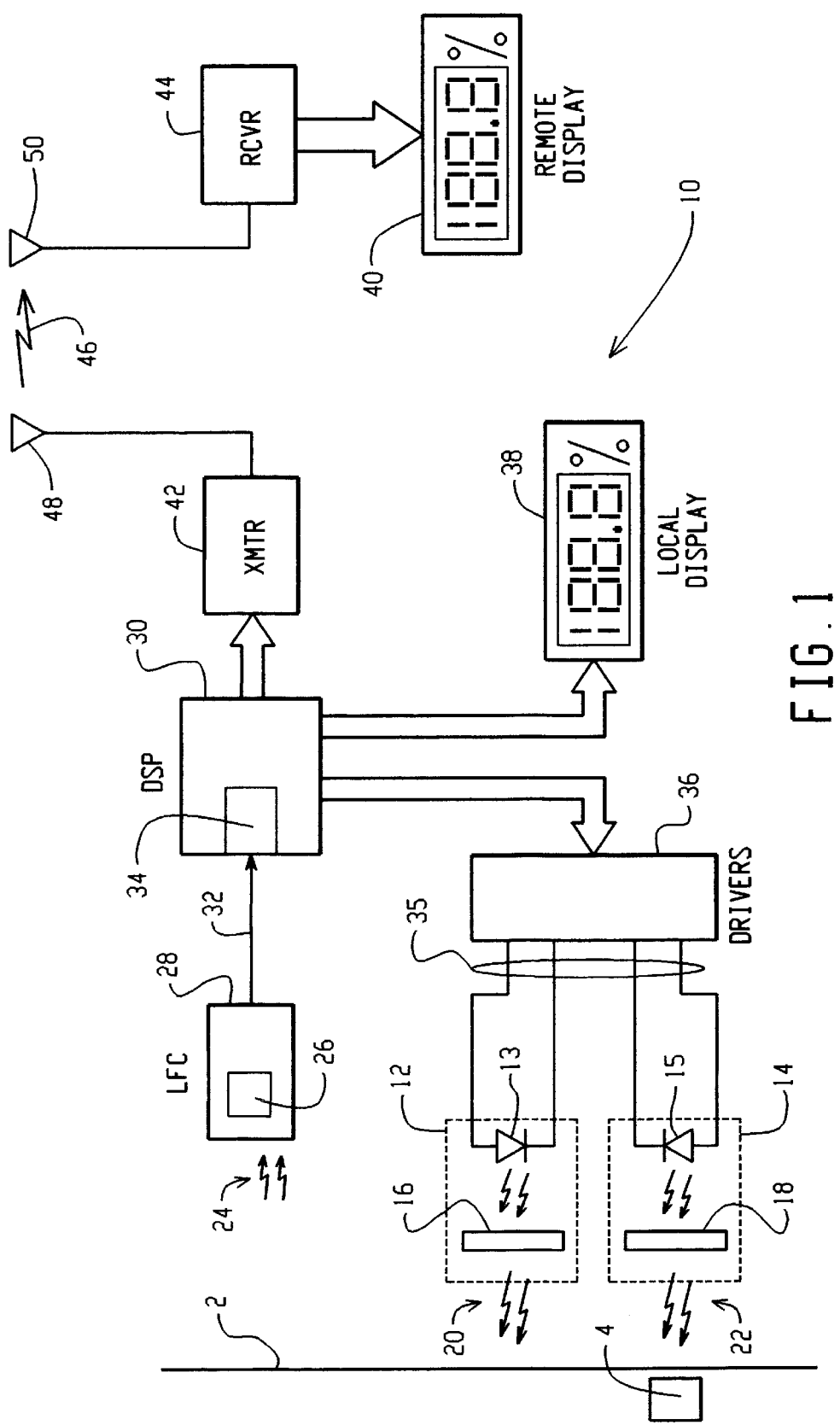
FIG. 1 is a block diagram of a pulse oximeter of the present invention.

Referring now more particularly to the accompanying drawings, FIG. 1 shows a pulse oximeter 10 according to the present invention. The oximeter 10 of the present invention comprises two emitters of green light 12, 14 that illuminate a volume of intravascular blood 4. The green light sources 12, 14 are shown schematically as including light emitting diodes (LEDs) 13, 15 in FIG. 1; however, other green light sources can be used, such as laser diodes, filtered white light sources, filtered broad-band LEDs, etc. Suitable LEDs 13, 15 include part. nos. TLGA-183P (peak wavelength 574 nm) and TLPGA-183P (peak wavelength 562 nm) from Toshiba Ltd. through various sources, such as Marktech International, 5 Hemlock Street, Latham, N.Y. 12110, (518) 786-6591. The wavelengths of light that can be used range from about 500 nm to about 600 nm.

Depending on the particular green light sources chosen, green optical filters 16, 18 might be needed. For example, if the Toshiba Ltd. part nos. TLGA183P and TLPGA-183P are used as green LEDs 13, 15 then narrow-band optical filters 16, 18 need to be used. Suitable optical filters include custom-made molded acrylic aspheric lens/filters having peak wavelengths of 560 nm and 580 nm, respectively, and which have bandwidths of less than 5 nm, which are available from Innovations In Optics, Inc., address 38 Montvale Avenue, Suite 215, Storeham, Mass. 02180, (716) 279- 0806. Also, depending on the particular green light sources used, more than one emitter of green light might be needed. For example, if green LEDs TLGA183P and TLPGA-183P are used, then one to four LEDs of each green frequency are needed.

Whichever particular green light sources are used, the green light 20 emitted from the first emitter of green light 12 must have a peak wavelength that is different than the peak wavelength of the green light 22 emitted by the second emitter of green light 14. Also, the wavelength bands of the green light emitted by the green light sources 12, 14 must be narrow enough that usably different signals are generated by the interaction between the light 20, 22 and the volume of intravascular blood 4. For example, either of two sets of wavelengths is equally functional: 542 and 560 nm or 560 and 577 nm. 560 and 577 nm are preferred due to current commercial availability.

Whichever peak wavelengths and wavelength bands are used, what is important is that electromagnetic radiation 20 from the first source 12 must have an absorption coefficient with respect to oxyhemoglobin that is substantially different (i.e., measurably different) than the absorption coefficient with respect to oxyhemoglobin of electromagnetic radiation 22 emitted by the second source 14. Likewise, if some other substance other than oxygen (e.g., carbon monoxide (HbCO)) is to be detected, what is important is that electromagnetic radiation 20 from the first source 12 must have an absorption coefficient with respect to the substance to be detected that is substantially different (i.e., measurably different) than the absorption coefficient with respect to the substance to be detected of electromagnetic radiation 22 emitted by the second source 14. If levels of oxygen and carbon monoxide saturation are to be detected, a third green wavelength is added to determine RHb, $HbO_2$, and HbCO components. These three components are then used to determine levels of oxygen and carbon monoxide saturation. Saturation of HbCO and other blood components is determined in a manner like $HbO_2$, as disclosed herein. In short, the two green light sources alternatively illuminate the blood and the resulting signals are placed in the frequency domain and used to determine a ratio (R) value. From the R value, the saturation value is determined using a look-up table.

The green light 20, 22 alternately illuminating the volume of intravascular blood 4 results in an optical signal 24 with a time-varying intensity reflected back from the intravascular blood 4 for each of the wavelengths. The resulting signal 24 comprises the data needed to determine the saturation of oxygen in the hemoglobin. The signal 24 is detected by an optical detector 26 such as a photodiode 26 of a light-to-frequency converter (LFC) 28, which is interfaced to a processor 30 via an LFC signal line 32. The LFC signal is input into a counter 34, which is in circuit communication with the processor 30.

Figure 2:
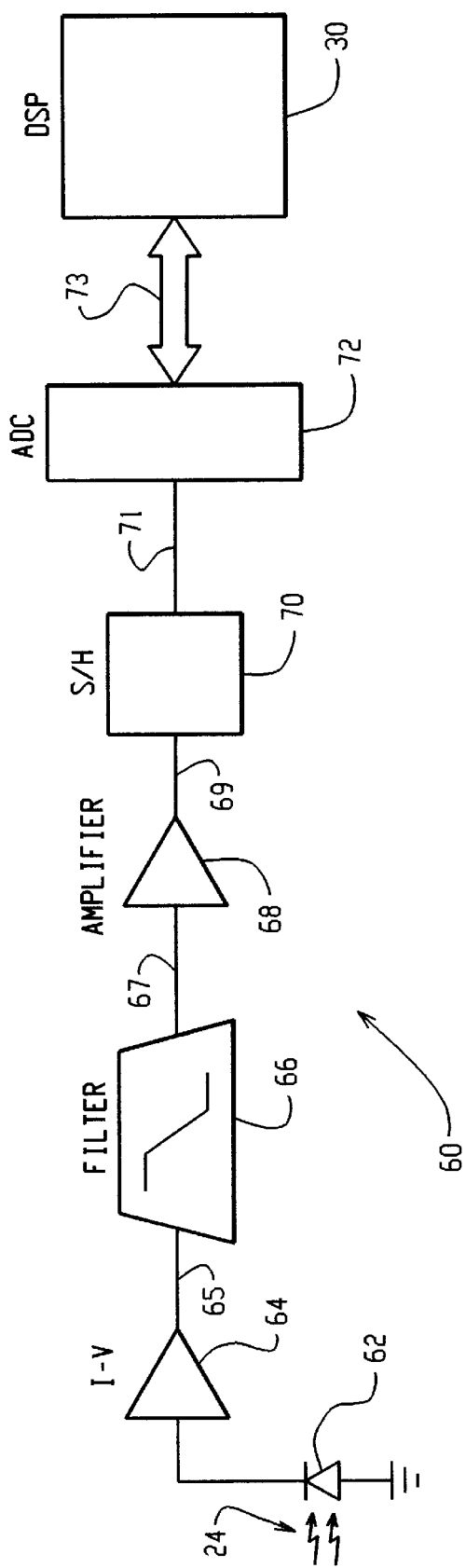
FIG. 2 is a block diagram of an alternative circuit of a pulse oximeter of the present invention.
Figure 3:
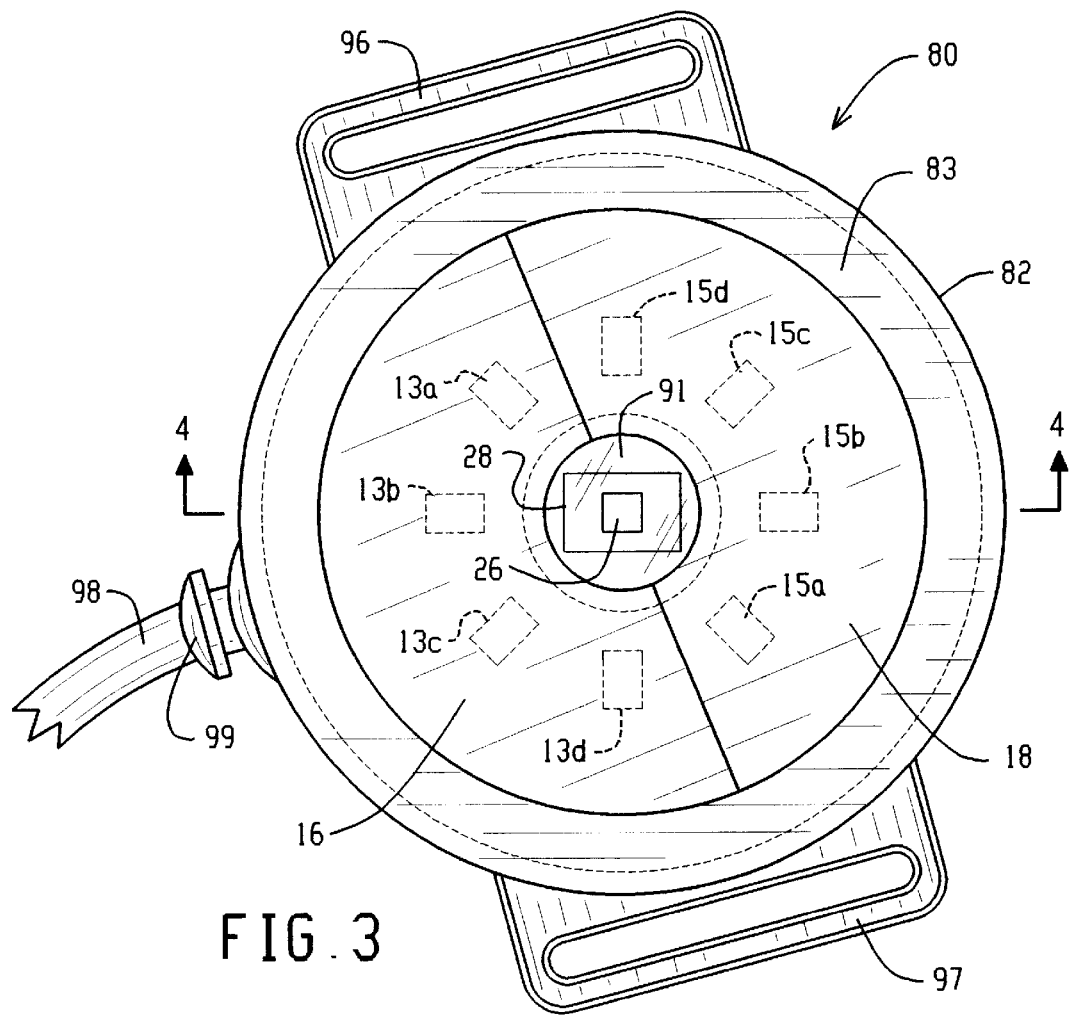
FIG. 3 is a bottom plan view of an oximeter probe according to the present invention.
Figure 4:
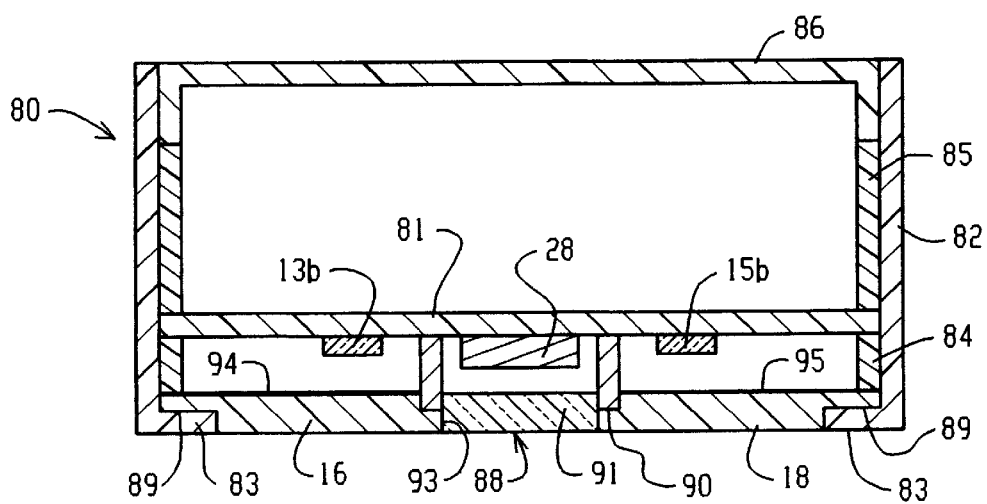
FIG. 4 is a sectional view taken substantially along the plane designated by the line 4—4 of FIG. 3.
Figure 5:
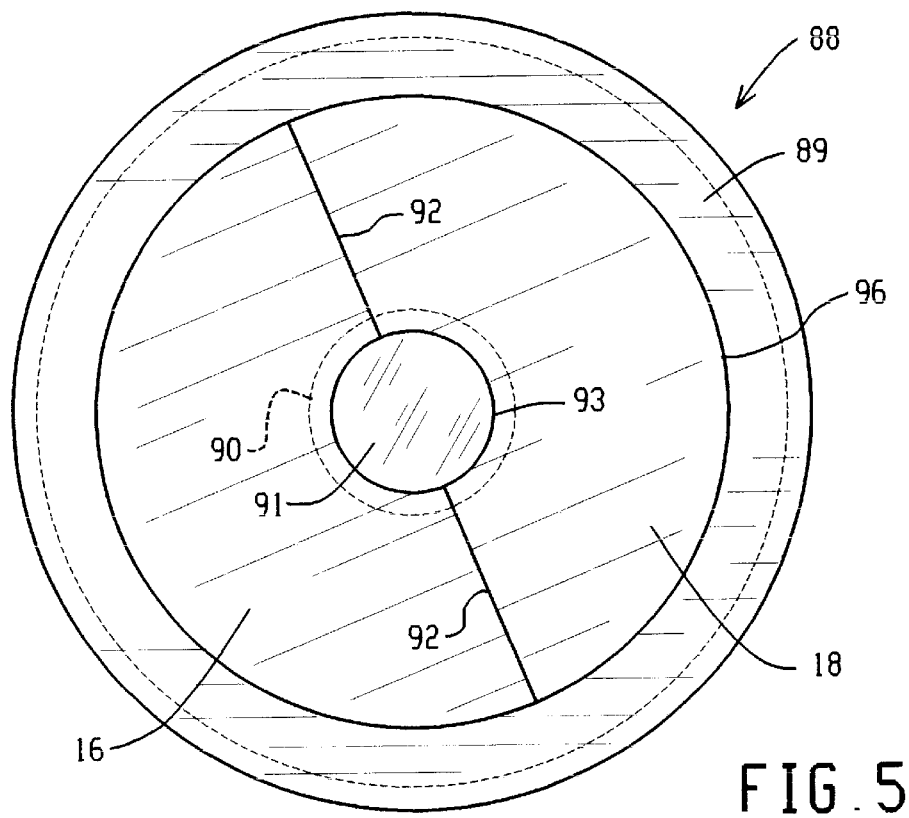
FIG. 5 is a bottom plan view of a face 88 of the oximeter probe of FIGS. 3 and 4.
Figure 7:
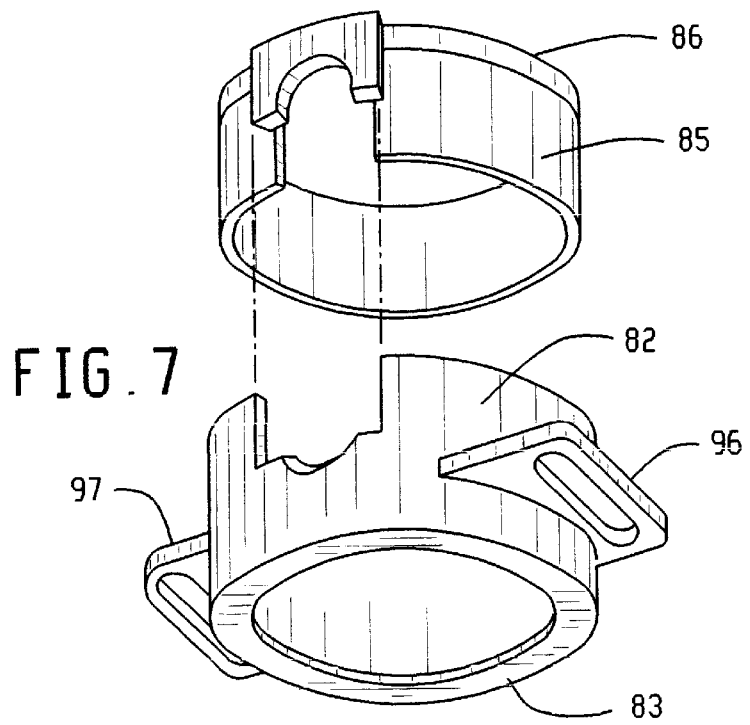
FIG. 7 is an enlarged partially exploded view showing the housing and housing spacer of the oximeter probe of FIGS. 3 and 4.
Figure 6:
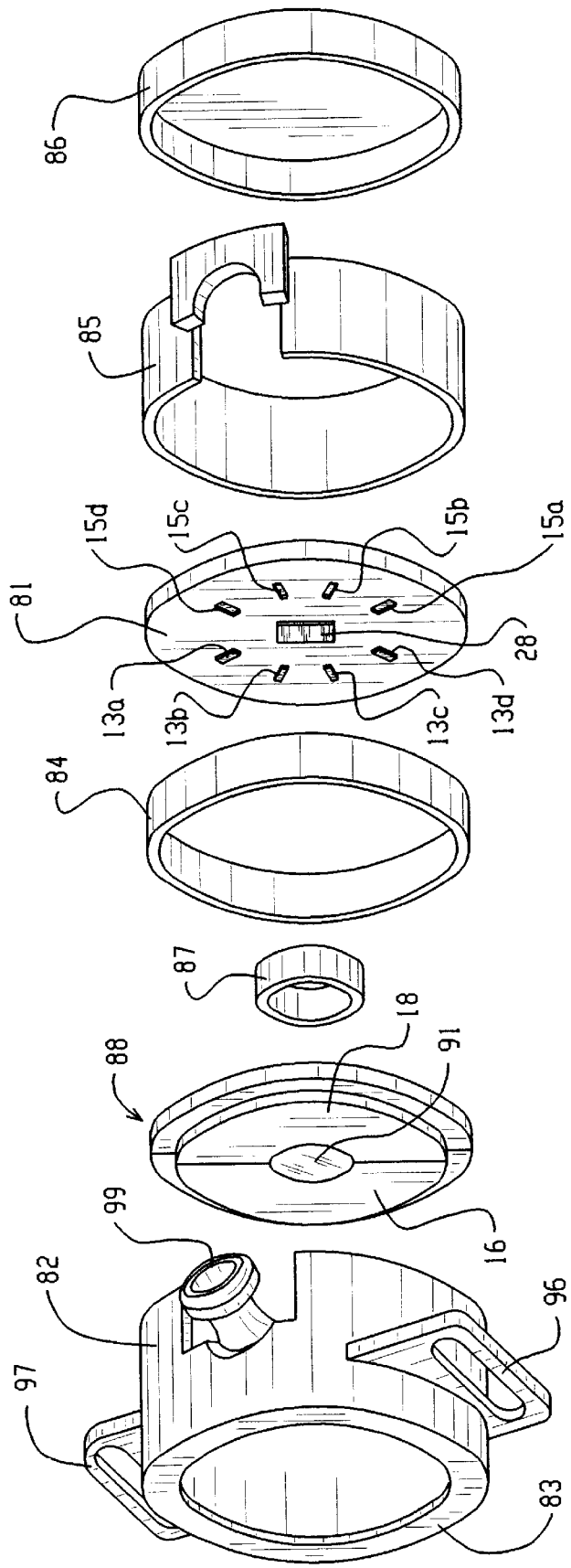
FIG. 6 is an exploded view of the oximeter probe of FIGS. 3 and 4.

The LFC 28 produces a periodic electrical signal in the form of a pulse train having a frequency corresponding to the intensity of the broadband optical signal received by the LFC 28. One suitable LFC 52 is the TSL235, manufactured and sold by Texas Instruments, P.O. Box 655303, Dallas, Tex. 75265. Other LFCs in Texas Instruments' TSL2XX series may also be used. Using an LFC eliminates the need for a separate silicon photodiode, a current-to-voltage converter (a transimpedance amplifier), a preamplifier, filter stage, a sample and hold, and an analog-to-digital (A/D) converter to capture the oximetry signal. As shown in FIG. 2, and described below in the text accompanying FIG. 2, these components can be used in the alternative.

Referring back to FIG. 1, the counter 34 may be an external counter or a counter internal to the processor 30, as shown in FIG. 1. If the counter 34 is an external counter, any high speed counter capable of being interfaced to a processor may be used. One suitable counter is the 4020 CMOS counter, which is manufactured by numerous manufacturers, e.g., Texas Instruments, P.O. Box 655303, Dallas, Tex. 75265, as is well known in the art.

The processor 30 may be any processor that can process oximetry data in real time and interface and control the various devices shown in FIG. 1. One suitable processor is a PIC17C43 8-bit CMOS EPROM microcontroller, which is available from Microchip Technology Inc., address 2355 West Chandler Blvd., Chandler, Ariz. 85224-6199, (602) 786-7668. Another suitable processor is the TMS320C32 digital signal processor, also manufactured by Texas Instruments. Another suitable processor is a Zilog 893XX. These processors have internal counters 34. Many other CISC and RISC microprocessors, microcontrollers, and digital signal processors can be used. Some might require random access memory (RAM), read-only memory (ROM), and associated control circuitry, such as decoders and multi-phase clocks, floating point coprocessors, etc. (all not shown) all in circuit communication, as is well known in the art. To be suitable, the processor 30 must be capable of being a signal analyzer. That is, the processor 30 must have the computational capacity to determine the saturation value from the collected data (LFC periodic pulses or ADC data, etc.).

Interfacing the counter 34 and the processor 30 may be done in several ways. The counter 34 and processor 30 may be configured to either (1) count the pulses generated by the LFC 28 during a given time period or (2) count the number of pulses of a free-running clock (corresponding to the amount of time) between the individual pulses of the LFC 28. Either method will provide satisfactory data. The latter method can be implemented in several ways. For example, the counter can be reset at each period of the LFC signal. In the alternative, at each edge of LFC pulse train, the value in the counter can be saved to a register and subtracted from the value stored at the previous edge. Either way, the result is a counter value corresponding to the time difference between the two pulse edges. Many other configurations are possible. The counter 34 can either count pulses or elapsed time between edges and the processor 30 either reads the value in the counter periodically by polling the counter, or the processor 30 reads the value whenever the counter 34 generates an interrupt. Again, many other configurations are possible.

Green light sources 12, 14 are driven along green light source power driver lines 35 by drivers 36. Although four green light source power driver lines 35 are shown for clarity, in the alternative there need be only two such lines and they and the sources 12, 14 are electrically connected such that only one source emits green light if one of the two driver lines is grounded and the other is at, e.g., +5 VDC (current limited), and vice versa. For example, if the sources 12, 14 are diodes 13, 15, then the cathode of diode 13 is connected to the anode of diode 15, the anode of diode 13 is connected to the cathode of diode 15, and the two nodes are connected via green light source power driver lines 35 to current-limited drivers 36.

The drivers 36 drive the sources 12, 14 at the required voltage and current in an alternating manner, as known to those skilled in the art. If sources 12, 14 include LEDs 13, 15, then several suitable driver configurations, known to those skilled in the art, are available to drive the LEDs 13, 15 at the required voltage and current. For example, a 74, 74H, or 74S family buffer or inverter, such as a 7400 can be used to directly drive LEDs with suitable current limiting resistors (all not shown). As another example, it is common to drive LEDs from CMOS, NMOS, 74LS, or 74HC family devices with an NPN or PNP transistor such as a 2N2222 with suitable current limiting resistors (all not shown). Both drivers are widely known to those in the art. Additionally, constant current drivers 36 for LEDs 13, 15 will tend to produce a constant brightness from the LEDs 13, 15. The exact parameters of the driver will depend on the particular sources 12, 14 selected and are available from common sources.

What is critical about the drivers 24 is that they properly drive the sources 12, 14 and that they be interfaced with the processor 30 in such a way that oximetry data is gathered. For example, the processor 30 might actually control the alternate illumination of the green sources 12, 14 by actively controlling the drivers 36. As another example, the drivers 36 might have a local oscillator (not shown) that causes the sources 12 14 to alternatively illuminate the patient's skin 2 and the processor would then receive a timing signal relating to which source is currently illuminating.

Some drivers 36 might need a normalizing function that increases or decreases the intensity of electromagnetic radiation generated by the light sources 12, 14 in the system. For example, it might be desirable to be able use a single oximeter configuration to measure the oxygen saturation of an infant and later to use the same oximeter configuration to measure oxygen saturation levels of an adult. Since the nature of skin 2 and hair of an infant are different from that of an adult, it is generally accepted that an LED intensity calibrated to measure the oxygen saturation level of an adult will be too bright to measure the oxygen saturation level of an infant (the optical signal 24 is so bright that the photodiode 26 saturates). Likewise, it is generally accepted that a light intensity calibrated to measure saturation of an infant will be too dim to provide adequate data to measure the oxygen saturation of an adult or a person with heavily pigmented skin 2. The normalizing function adjusts the intensities of the sources 12, 14 to provide a useful signal under most circumstances.

In the oximeter 10 of the present invention, the normalizing function might be not needed if an LFC is used. The TSL235 has a dynamic range of approximately 118 dB. Moreover, the TSL230 is an LFC with a computer-interfacable gain control for amplification or attenuation of the optical signal, thereby providing an even higher dynamic range. These very wide dynamic ranges allow the use of drivers 36 to be configured such that the intensities of the light sources 12, 14 are set at fixed, predetermined values. Said another way, these LFCs are so sensitive that an light intensity suitable for an infant might still generate a reflected optical signal 24 in an adult strong enough to determine the saturation value of that adult. Thus, the drivers 36 might not need to have the ability to normalize the intensities of the sources 12, 14.

Preferably, the processor 30 is in circuit communication with a local display 38 to display a visual image corresponding to the oximetry data. The local display 38 can be any display capable of displaying a visual image corresponding to one or more oxygen saturation values at the desired resolution. The local display 38 can display any number of different visual images corresponding to the oximetry data. For example, a simple numeric liquid crystal display (LCD) can be used to numerically display the saturation value. In the alternative, or in addition, a graphical LCD can be used to display the saturation value and display the pulse plethysmograph waveform. In addition, discrete display LEDs (not shown) may be used if the designer desires to display merely a binary oxygen saturation level. For example, green, yellow, and red discrete LEDs can be configured to represent safe, critical, and emergency conditions corresponding to saturation values of greater than 90 percent, 70 to 90 percent, and less than 70 percent, respectively.

Preferably, the processor 30 is also in circuit communication with a remote display 40 to display a second visual image corresponding to the oximetry data. Like the local display, the remote display 40 can have any number of configurations. In addition to the displays listed above in connection with the local display 38, the remote display can be an integral part of a nurses' station receiver or some other personal data receiver. In the alternative, the remote receiver can be a standard personal computer (not shown) configured to display the desired image and numerical values.

The processor 30 and the remote display 40 are placed in circuit communication via a transmitter 42 and receiver 44. The transmitter 42 transmits a signal 46 using an antenna 48. The receiver 44 receives the signal 46 using a second antenna 50 and passes the information to the display circuit 40. The transmitter 42, receiver 44, and the two antennas 48, 50 can be any suitable radio frequency or other wireless telemetry system, including infrared, biomedical (49 MHz), or microwave systems. These telemetry systems are well known in the art and widely available from common sources. Additionally, spread spectrum technology (~900 MHz or 2.4 GHz) provides a highly secure link, a high noise immunity, and a high informational capacity, all of which are desirable in clinical and health care environments. A suitable 902–908 MHz or 2.4 GHz spread spectrum transmitter/receiver pair is available from common sources, such as Digital Wireless Corp., One Meczway, Norgrass, Ga., 30093 (transmitter) and Telxon Pen-Based Computer, 3330 W. Market Street, P.O. Box 5582, Akron, Ohio 44334-0582 (receiver).

Preferably, the transmitter 42 transmits the determined parameters, such as oxygen saturation, other gas saturation, pulse rate, respiration rate, etc. to the receiver 44, which requires a high level of digital signal processing capability at the sensor location. However, in the alternative, different data can be transmitted such as that has not been completely processed, e.g., the raw square-wave output 32 from the LFC 28 or digital words from the high speed counter. This alternative embodiment requires significantly less processing power at the sensor location.

Referring now to FIG. 2, an alternative oximeter 60 according to the present invention is shown. The use of green sources 12, 14 and drivers 36 are the same as FIG. 1. The optical signal 24 with the time-varying intensity is detected by a photodiode 62. The photodiode 62 generates a low-level current proportional to the intensity of the electromagnetic radiation received by the photodiode 62. The current is converted to a voltage by a current to voltage converter 64, which may be an operational amplifier in a current to voltage (transimpedance) configuration.

The resulting signal 65 is then filtered with a filter stage 66 to remove unwanted frequency components, such as any 60 Hz noise generated by fluorescent lighting. The filtered signal 67 is then amplified with an amplifier 68 and the amplified signal 69 is sampled and held by a sample and hold 70 while the sampled and held signal 71 is digitized with a high-resolution (e.g., 12-bit or higher) analog to digital converter (ADC) 72. The digitized signal 73 is then read from the processor 30.

Referring now to FIGS. 3–7, one embodiment of a probe 80 according to the present invention is shown. Surface mount LEDs 13a–13d and 15a–15d and the LFC 28 are mounted on a printed circuit board (PCB) 81. Surface mount LEDs 13a–13d can be part no. SML-010MTT86 (563 nm), from ROHM Corp., 3034 Owen Drive, Antioch, Tenn. 37013, which are available from Bell Industries, Altamente Springs, Fla. Surface mount LEDs 15a–15d can be part no. SSL-LXISYYC-RPTR from Lumex Optocomponents, Inc. (585 nm), which are available from Digikey Corp., 701 Brooks Avenue South, Thief River Falls, Minn. 56701-0677. The LEDs 13a–13d and 15a–15d are surface mounted in a roughly circular pattern around the LFC 28. The PCB 81 is mounted in a cylindrical housing 82 having an annular lip 83 projecting from one end. PCB 81 is held in place between a PCB spacer 84 and a housing spacer 85. A housing cap 86 closes off the other end of the housing 82. A light shield 87 shields the LFC 28 from direct illumination by the LEDs 13a–13d and 15a–15d. The PCB spacer 84 and the shield 87 engage a clear face 88, with the PCB spacer 84 engaging an outer surface 89 of the face 88 and the shield 87 positioned within an annular channel 90 cut into the face 88.

The face 88 comprises three sections: a clear, colorless area 91, a first filtered area 16, and a second filtered area 18. The filters 16, 18 are glued along a seam 92 with an appropriate optically clear adhesive, leaving a circular region into which the clear, colorless area 91 is glued at a circular seam 93. In the alternative, the face 88 can be made in a single piece (including pieces 16, 18, and 91) and coatings 94 and 95 can be used to implement the filters 16 and 18. Although shown as flat surfaces, face pieces 16, 18, and 91 can alternatively be shaped to form discrete lenses (not shown) to focus the radiant energy from the LEDs 13a–13d and 15a–15d onto the skin 2 and into the blood 4 and from the skin 2 onto the photodiode 26, 62. The face 88 steps down at an annular shoulder 96 to a thinner portion 89, which engages the lip 83 of the housing 82.

The PCB 81 can be made of common materials including fiberglass PCB material. The housing 82, PCB spacer 84, housing spacer 85, housing cap 86, and light shield 87 can all be injection molded of an opaque plastic such as several of the opaque injection-moldable plastics sold under the trademark "ZELUX." If made of one piece, the face 88 can be made of glass, which can endure the high temperature processing required to apply some narrowband coatings. One appropriate coating for coatings 94, 95 is a multilayer dielectric coating deposition (an ultra-narrowband coating) with a bandwidth of between 0.5 nm and 4.0 nm called MicroPlasma hard coating deposition, which is available through Innovations in Optics, Inc., 38 Montvale Ave, Suite 215, Stoneham, Mass. 02180, (617) 279-0806. These coatings 94, 95 are preferably centered at 560 nm and 577 nm, respectively, and have bandwidths of about 1.0 (one) nm.

The size of the probe is being reduced to watch-face/ wrist-band size having an approximately 1" diameter face of approximately ½" thickness.

The probe 80 also has two slotted tabs 96, 97 for reception of a strap (not shown) for securing the probe 80 against a body part. The strap can have hook and loop surfaces to facilitate securing and removing the probe 80. Additionally, the probe accepts a bundle of wires 98 to place the LEDs 13a–13d and 15a–15d and LFC 28 in circuit communication with the remaining circuitry of FIG. 1. The bundle of wires includes the LFC signal line 32 and the green light source power driver lines 35. Additionally, the bundle of wires includes +5 VDC and ground lines (not shown) for the TSL235 LFC 28. The individual wires of the bundle of wires 98 are secured to the PCB 81, and thereby electrically connected to the LEDs 13a–13d and 15a–15d and LFC 28, by soldering the wires to pads (not shown), wire wrapping the wires to pins (not shown), individual connectors, or other common methods known to those skilled in the art. A connector (not shown) at the other end of the bundle of wires 98 facilitates connection of the bundle of wires to an enclosure (not shown) which houses a processor PCB (not shown), upon which the processor 30, drivers 36, local display, and transmitter 42 are placed into circuit communication. A grommet 99 is retained between the housing 82 and the housing spacer 85 to provide stress/stain relief between bundle of wires and the sensor probe head.

Figure 8:
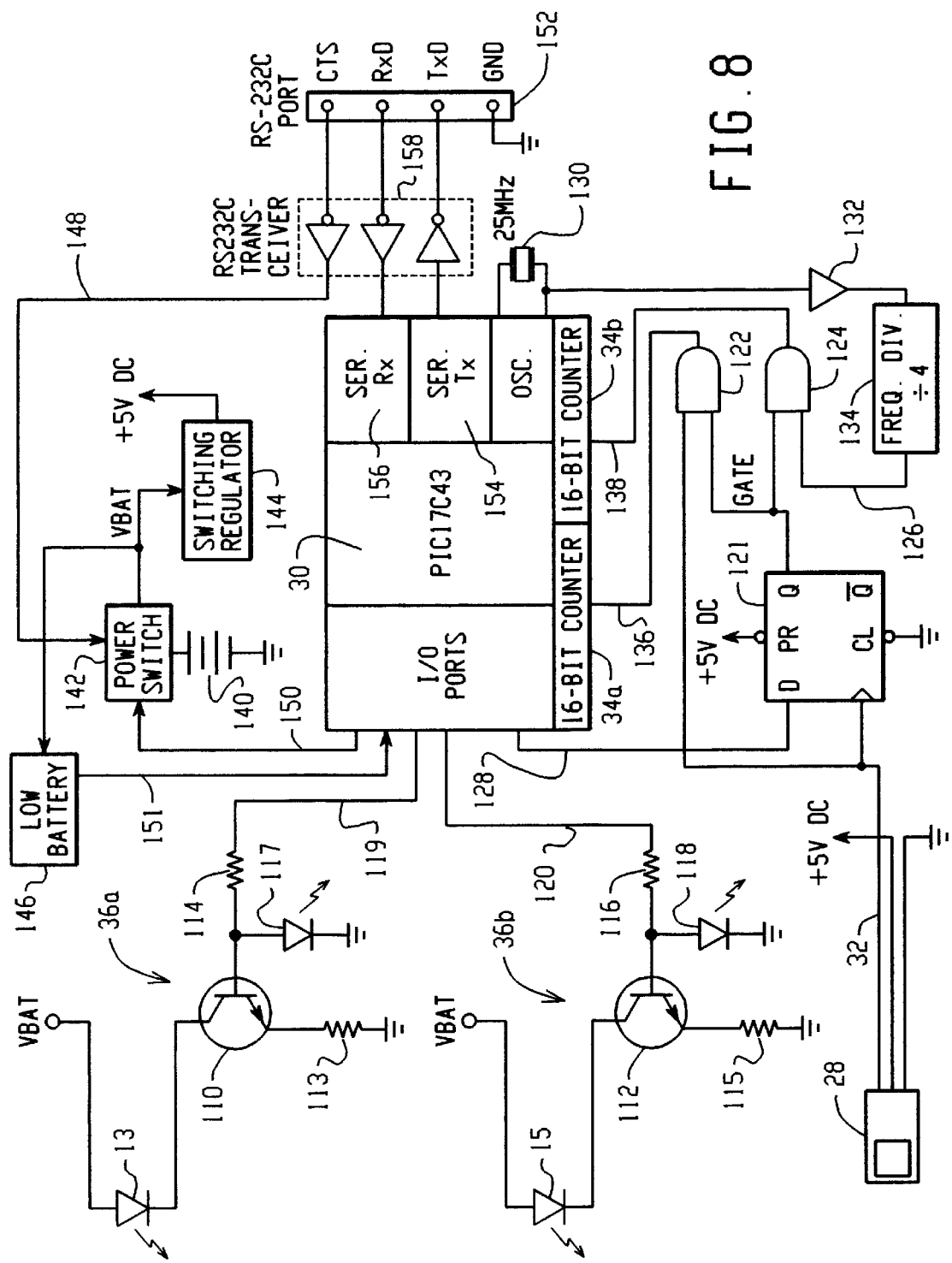
FIG. 8 is a schemato-block diagram showing the interface between the processor, the LED drivers, and the light-to-frequency converter of the pulse oximeter of present invention.

Referring now to FIG. 8, the interface between the processor 30, the LEDs 13, 15, and the LFC 28 are shown. Drivers 36a and 36b are constant current LED drivers driving LEDs 13, 15. Drivers 36a, 36b comprise NPN transistors 110 and 112, current limiting resistors 113–116, and LEDs 117 and 118, all of which are in circuit communication as shown in FIG. 8. The values of resistors 113–116 depend on the voltage drop and current requirements of the particular LEDs 13, 15 chosen and can be readily determined by those skilled in the art. Drivers 36a, 36b are controlled by I/O ports 119 and 120 of the processor 30.

The LFC 28 is electrically connected to two 16-bit counters 34a, 34b that are internal to the processor 30. The counters are arranged in a computing counter configuration using a falling edge-triggered D-type flip flop 121, two logic gates 122, 124, a high speed free-running clock 126, and a control line 128 from the processor 30. The high speed clock 126 is generated from a crystal oscillator 130, a buffer 132, and a frequency divider 134 (if needed). These components are in circuit communication as shown in FIG. 8.

The flip flop 121 and the logic gates 122, 124 function with the control signal to produce gated LFC signal 136 and gated clock signal 138. The control signal 128 becomes active a predetermined period of time (e.g., 0.5 ms) after the processor 30 activates one of the drivers 36. The first falling edge of the LFC signal 32 after the control signal 128 is asserted begins the gate period. During the gate period, the LFC signal 32 is passed through logic gate 122 to counter 34a via the gated LFC signal line 136. The number of rising edges of the gated LFC signal 136 are counted by counter 34a. Also during the gate period, the clock signal 126 is passed through logic gate 124 to counter 34b via the gated clock signal line 138. The number of rising edges of the gated clock signal 138 are counted by counter 34b. Then the frequency of the LFC signal, which is related to the intensity of the signal 24 received by the LFC 28, is determined by dividing the number of rising edges of the gated LFC signal 136 by the number of rising edges of the gated clock signal 138 and multiplying that result by the frequency of the clock 126. It will be readily apparent to those skilled in the art that other edges and other entire configurations could also be used.

After the control signal 128 is negated, the next falling edge of the LFC signal 32 ends the gate period; therefore, a minimum frequency for the LFC signal 128 must be assumed and the control signal 128 must be negated early enough that if the LFC signal is at its assumed minimum frequency, the gate period will be closed (a falling edge of the LFC signal 32 will arrive) before the processor causes the active driver to cease driving the illuminating LED. Also, if a final falling edge of the LFC signal does not occur within a predetermined period of time (e.g., 10 ms) after the control signal is enabled, then an error state can be entered. As discussed below, this process is alternately, repeatedly performed for each light source 12, 14.

FIG. 8 also shows a block diagram of the power components of the oximeter 10 of the present invention: a battery 140, a power control switch 142, a switching regulator 144, and a low battery detector 146, all in circuit communication as shown in FIG. 8. The power control switch 142 accepts as inputs a transceived CTS signal 148 and a control line 150 from the processor 30. The power control switch 142 also can accept an input from a switch (not shown) that can be, e.g., made as part of a probe according to the present invention or physically annexed to the oximeter enclosure (not shown). The switching regulator 144 generates +5 VDC from the battery voltage, VBAT. That is, the switching regulator 144 provides regulated voltages for the electronic devices from the battery or, alternatively, an external power source (not shown), as known to those skilled in the art. The low battery detector 146 detects when the battery voltage VBAT is at a voltage indicative of the end of the lifetime of the battery 140 or that the battery needs to undergo a charging from a battery charger (not shown). Once detected, the low battery detector 146 transmits a corresponding signal 151 to the processor 30 so the processor 30 can take appropriate action such as indicating a low battery condition via the display(s) 38, 40 or turning the oximeter 10 off to protect system components from an undervoltage situation. Finally, FIG. 8 shows the implementation of an RS-232C serial port 152 using serial transmit 154 and serial receive 156 ports of the processor 30 and an RS-232C transceiver 158 to transmit and receive RS-232C signals at a proper RS-232C level. The RS-232C port 152 can be used to upload to, e.g., a personal computer the numeric counts for the number of rising edges of the gated LFC signal 136 for each source 12, 14 and the number of rising edges of the gated clock signal 138 for each source 12, 14. One possible transmission format for transmitting data from the processor 30 to a personal computer includes a synchronizing byte, 16 bits of gated LFC signal data for the first source 12, 16 bits of gated clock data for the first source 12, 16 bits of gated LFC signal data for the second source 14, 16 bits of gated clock data for the second source 14, a status byte (e.g., overflow indication, battery condition, etc.), and a parity byte.

Figure 9:
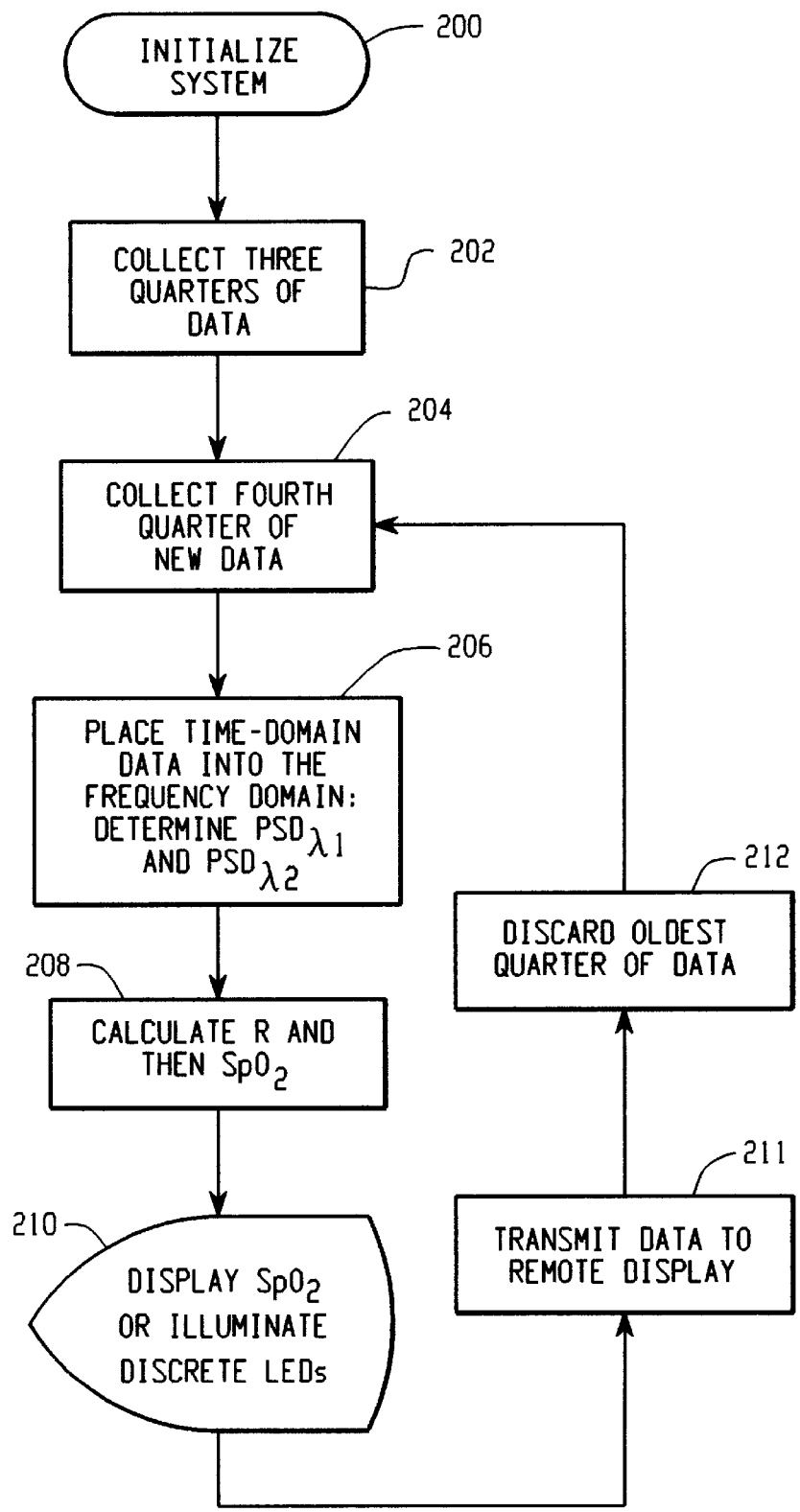
FIG. 9 is a flow chart showing the major process steps taken by the processor in calculating the saturation value.

Referring now to FIG. 9, a flow chart showing the role of the processor 30 in the pulse oximeter 10 of the present invention is shown. Essentially, the processor 30 collects data in the form of a digitized signal, calculates a coefficient for the oxygen saturation value from the digitized signal, determines the final saturation value by reading the saturation value for the calculated coefficient from a look-up table stored in memory, and then causes the display(s) 38, 40 to display a visual image corresponding to the final saturation value or other oximetry data.

When either of the sources 12, 14 is emitting and a signal 24 is being generated by the interaction of the electromagnetic radiation with the blood 4, the LFC 28 generates a periodic electrical signal in the form of a pulse train with a period corresponding to the intensity of the optical signal 24 received by the LFC 28. This signal 24 is interfaced into the processor 30 with the counter 34, as described above, and an intensity value for the first green light source 12 and an intensity value for the second green light source 14 are determined and saved in RAM.

First, the processor 30 initializes the system, at 200. Such initialization might include initializing data structures, initializing timers, initializing counters, initializing prescalars, initializing interrupts etc. and is very system-specific as is known to those in the art. After initializing the system, the processor 30 begins collecting samples of data. A "sample" is the reading of two intensity values with the LCF 28 and counter 34: (1) an intensity value with the first green light source 12 constantly emitting and the second green light source 14 not emitting and (2) an intensity value with the second green light source 14 constantly emitting and the first green light source 12 not emitting, both as further described in the text accompanying.g., FIGS. 3 and 8.

Preferably, one sample of data is collected as follows. First, the processor 30 causes the drivers 36 to cause the first green emitter 12 to emit (turn on) and the second green emitter 14 to not emit (turn off) for approximately 15 milliseconds. During this 15 milliseconds, the processor 30 receives pulses from the LFC 28 via the counters 34a, 34b. Next, the processor stores the values counted by the counters 34a, 34b. Then the processor 30 causes the drivers 36 to cause the first green emitter 12 to turn off and the second green emitter 14 to turn off for approximately 1 millisecond. During this 1 ms, outputs from the LFC 28 are ignored by the processor 30. Then the processor 30 causes the drivers 36 to cause the first green emitter 12 to turn off and the second green emitter 14 to turn on for approximately 15 milliseconds. During this 15 milliseconds, the processor 30 receives pulses from the LFC 28 via the counters 34a, 34b. Next, the processor stores the values counted by the counters 34a, 34b. Finally, the processor 30 once again causes the drivers 36 to cause both green emitters 12, 14 to turn off for approximately 1 millisecond. During this 1 ms, outputs from the LFC 28 are ignored by the processor 30. This process is repeated indefinitely.

Data collection begins at 202. The total data collection period is 4.27 seconds in this embodiment, which is divided into four quarters of approximately one second each. As shown at 202, three quarters (approximately three seconds) of data samples are collected to help initialize a sliding window function, described below. Next, the fourth quarter of the total sample (approximately one second worth of samples) is taken, at 204. The sample rate and time of collection are all variable; preferable values are given above. In this embodiment, between the samples taken at 202 and 204, a total of 4.27 seconds worth of samples are collected for processing. As discussed above in connection with FIG. 8, the samples are taken every 32 milliseconds. However, the samples can be taken at many rates, e.g., about 15 hertz to about 240 Hz, depending on the processing to take place, as is known in the art.

The processor 30 then converts the 4.27 seconds of time-domain data into the frequency domain 206 by, e.g., performing the well-known Fast Fourier Transform (FFT). The FFT can be implemented in many ways, as is known in the art. For example, an FFT of between 64 points (on data sampled at 15 Hz) and 1024 points (on data sampled at 240 Hz) will suffice. From the frequency-domain data, the processor 30 then determines the saturation value using any of several algorithms known to those skilled in the art. For example, the power spectral density (PSD) of the cardiac (~1 Hz) spectral line and power spectrum estimation (PSE) are believed to be suitable algorithms.

In the case of the power spectral density, the PSD for the wavelength of the light from the first source 12 ($PSD_{\lambda 1}$) and the PSD for the wavelength of the light from the second source 14 ($PSD_{\lambda 2}$) are determined at about 1 hertz (the cardiac spectral line). Then, $R=(PSD_{\lambda 1})/(PSD_{\lambda 2})$ and R can be used to derive the saturation value from a lookup table in memory, as is known to those in the art. The lookup table can be derived by those in the art from widely available hemoglobin spectral absorption curves and experimental empirical data. For example, using 577 and 560 nm light sources and using $R=(PSD_{\lambda 1=577\ nm})/(PSD_{\lambda 2=560\ nm})$ at the cardiac spectral line, the following table can be used to determine the oxygen saturation level from the ratio R:

| R | $SpO_2$ |
|---|---|
| 0.74 | 0 |
| 0.82 | 10 |
| 0.90 | 20 |
| 0.98 | 30 |
| 1.08 | 40 |
| 1.18 | 50 |
| 1.28 | 60 |
| 1.40 | 70 |
| 1.53 | 80 |
| 1.67 | 90 |
| 1.82 | 100 |

As is known in the art, in the alternative to the FFT, many other methods can be used to place the data in the frequency domain. For example, it is believed that the well known discrete cosine transform, wavelet transform, discrete Hartley transform, Short-Time Fourier Transform (STFT), and Gabor Spectrogram can all be used.

Next, the calculated saturation value is displayed on the display 38, as described above and known in the art, at 210. Contemporaneously therewith, at 211, the determined saturation value (and any other data to be displayed on the remote display 40) is written by the processor 30 to the transmitter 42, transmitted by the transmitter 42, received by the receiver 44, and displayed on the remote display 40.

Finally, the program loops back to 204, where another one quarter of 4.27 seconds of data is collected. As indicated at 212, the oldest quarter of data is discarded so that 4.27 seconds of data remain (only approximately one second of which is new). Thus a 4.27 second window of data can be thought of as sliding by one-quarter increments, thereby discarding approximately one second of data and sampling a new one second of data. The steps at 204, 206, 208, 210, and 212 are performed repeatedly, thereby determining and displaying a new SpO$_2$ value approximately each second.

Using the green light pulse oximeter of the present invention is straightforward. Although normalization is generally not needed because of the wide dynamic range of the LFC 28, if any calibration or normalizing of the light sources 12, 14 is to be done, this calibration or normalization is done before any measurements are taken. Then the probe 80 is secured to the patient with a strap having hook and eye surfaces using the slotted tabs 96, 97. The probe can also be secured with two-sided skin adhesive or a bulb suction apparatus (both not shown). Once the probe is in place, the processor begins the processing described in, e.g., the text accompanying FIGS. 8 and 9, which determines, transmits, and displays the saturation value and any other desired values.

The present invention has wide utility. Virtually any reflectance pulse oximeter design could be modified to use the green light sources 12, 14 of the present invention. Therefore, the invention in its broader aspects is not limited to the specific details, representative apparatus and method, and illustrative examples shown and described. Accordingly, departures may be made from such details without departing from the spirit or scope of the applicant's general inventive concept.

Thus, while the present invention has been illustrated by the description of embodiments thereof, and while the embodiments have been described in considerable detail, it is not the intention of the applicant to restrict or in any way limit the scope of the appended claims to such detail. Additional advantages and modifications will readily appear to those skilled in the art. For example, other light-to-frequency converters can be used. As another example, a 2048-point FFT can be performed on 8.53 seconds of data collected at 240 Hz. Finally, with minor modifications to the signal analysis portion of this system, the present invention can be used as a diagnostic instrument for determining other cardiovascular system parameters, such as pulse rate, respiration rate, intravascular volume status, and saturation of other gases, such as carbon monoxide. Therefore, the invention in its broader aspects is not limited to the specific details, representative apparatus and method, and illustrative examples shown and described. Accordingly, departures may be made from such details without departing from the spirit or scope of the applicant's general inventive concept.

I claim:

1. A pulse oximeter for determining the oxygen saturation of hemoglobin, comprising:
   (a) a first emitter of green light for selectively illuminating a skin surface and a volume of intravascular blood therebeneath;
      the green light from said first emitter of green light having a first peak wavelength and a first wavelength band associated therewith;
      said first peak wavelength being within the range of about 500–600 nm;
      light at said first peak wavelength having absorption coefficients with respect to oxyhemoglobin and deoxyhemoglobin;
      the green light from said first emitter of green light interacting with oxyhemoglobin in the volume of intravascular blood, thereby generating a first optical signal, the first optical signal having an intensity;
   (b) a second emitter of green light for selectively illuminating the skin surface and the volume of intravascular blood therebeneath;
      the green light from said second emitter of green light having a second peak wavelength and a second wavelength band associated therewith;
      said second peak wavelength being within the range of about 500–600 nm;
      light at said second peak wavelength having absorption coefficients with respect to oxyhemoglobin and deoxyhemoglobin;
      at least one of the absorption coefficients of light at said first peak wavelength being different than the respective absorption coefficient of light at said second peak wavelength;
      the green light from said second emitter of green light interacting with deoxyhemoglobin in the volume of intravascular blood, thereby generating a second optical signal;
      the second optical signal having an intensity;
   (c) an electromagnetic radiation sensor electrically connected to an electronic signal generator;
      said electromagnetic radiation sensor adapted to be optically coupled to the skin surface for reception of the first and second optical signals;
      said electronic signal generator generating an electrical signal responsive to said electromagnetic radiation sensor, the electrical signal corresponding to the intensity of the optical signal being received by said electromagnetic sensor; and
   (d) a signal analyzer connected to said electronic signal generator for determining from the electrical signal the oxygen saturation of the hemoglobin within the volume of blood.

2. A pulse oximeter according to claim 1 wherein said first peak wavelength is about 560 nm and said second peak wavelength is about 577 nm.

3. A pulse oximeter according to claim 2 wherein said first and second wavelength bands are less than or equal to 5 nm wide.

4. A pulse oximeter according to claim 2 wherein said first and second wavelength bands are about 1 nm wide.

5. A pulse oximeter according to claim 2 wherein said signal analyzer determines the oxygen saturation of the hemoglobin within the volume of intravascular blood without using any parameter determined from interaction between the volume of intravascular blood and electromagnetic radiation within at least one of the red and infrared regions of the electromagnetic spectrum.

6. A pulse oximeter according to claim 5 wherein said signal analyzer performs a method for determining the oxygen saturation of the hemoglobin comprising the steps of:
   (a) collecting a first plurality of data values corresponding to a plurality of first optical signal intensities;
   (b) collecting a second plurality of data values corresponding to a plurality of second optical signal intensities; and
   (c) analyzing the first and second pluralities of data values in the frequency domain to determine the oxygen saturation of the hemoglobin.

7. A pulse oximeter according to claim 2 wherein said signal analyzer performs a method for determining the oxygen saturation of the hemoglobin comprising the steps of:
   (a) collecting a first plurality of data values corresponding to a plurality of first optical signal intensities;
   (b) collecting a second plurality of data values corresponding to a plurality of second optical signal intensities; and (c) analyzing the first and second pluralities of data values in the frequency domain to determine the oxygen saturation of the hemoglobin.

8. A pulse oximeter according to claim 1 wherein said first and second wavelength bands are less than or equal to 5 nm wide.

9. A pulse oximeter according to claim 1 wherein said first and second peak wavelengths are within the range of about 540–577 nm.

10. A pulse oximeter according to claim 6 wherein said first and second wavelength bands are less than or equal to 5 nm wide.

11. A pulse oximeter according to claim 6 wherein said first and second wavelength bands are about 1 nm wide.

12. A pulse oximeter according to claim 6 wherein said signal analyzer determines the oxygen saturation of the hemoglobin within the volume of intravascular blood without using any parameter determined from interaction between the volume of intravascular blood and electromagnetic radiation within at least one of the red and infrared regions of the electromagnetic spectrum.

13. A pulse oximeter according to claim 11 wherein said signal analyzer performs a method for determining the oxygen saturation of the hemoglobin comprising the steps of:

(a) collecting a first plurality of data values corresponding to a plurality of first optical signal intensities;

(b) collecting a second plurality of data values corresponding to a plurality of second optical signal intensities; and (c) analyzing the first and second pluralities of data values in the frequency domain to determine the oxygen saturation of the hemoglobin.

14. A pulse oximeter according to claim 6 wherein said signal analyzer performs a method for determining the oxygen saturation of the hemoglobin comprising the steps of:

(a) collecting a first plurality of data values corresponding to a plurality of first optical signal intensities;

(b) collecting a second plurality of data values corresponding to a plurality of second optical signal intensities; and (c) analyzing the first and second pluralities of data values in the frequency domain to determine the oxygen saturation of the hemoglobin.

15. A pulse oximeter according to claim 1 wherein said signal analyzer determines the oxygen saturation of the hemoglobin within the volume of intravascular blood without using any parameter determined from interaction between the volume of intravascular blood and electromagnetic radiation within at least one of the red and infrared regions of the electromagnetic spectrum.

16. A pulse oximeter according to claim 9 wherein said signal analyzer performs a method for determining the oxygen saturation of the hemoglobin comprising the steps of:

(a) collecting a first plurality of data values corresponding to a plurality of first optical signal intensities;

(b) collecting a second plurality of data values corresponding to a plurality of second optical signal intensities; and (c) analyzing the first and second pluralities of data values in the frequency domain to determine the oxygen saturation of the hemoglobin.

17. A pulse oximeter according to claim 1 wherein said first and second emitters of green light each comprise a source of electromagnetic radiation and an optical bandpass filter.

18. A pulse oximeter according to claim 1 wherein said signal analyzer performs a method for determining the oxygen saturation of the hemoglobin comprising the steps of:

(a) collecting a first plurality of data values corresponding to a plurality of first optical signal intensities;

(b) collecting a second plurality of data values corresponding to a plurality of second optical signal intensities; and (c) analyzing the first and second pluralities of data values in the frequency domain to determine the oxygen saturation of the hemoglobin.

19. A pulse oximeter probe for use with a pulse oximeter for determining the oxygen saturation of hemoglobin, comprising:

(a) a probe housing;

(b) a first emitter of green light for selectively illuminating a skin surface and a volume of intravascular blood therebeneath, said first emitter of green light being physically annexed to said probe housing;

the green light from said first emitter of green light having a first peak wavelength and a first wavelength band associated therewith;

said first peak wavelength being within the range of about 500–600 nm;

light at said first peak wavelength having absorption coefficients with respect to oxyhemoglobin and deoxyhemoglobin;

the green light from said first emitter of green light interacting with oxyhemoglobin in the volume of intravascular blood, thereby generating a first optical signal, the first optical signal having an intensity;

(c) a second emitter of green light for selectively illuminating the skin surface and the volume of intravascular blood therebeneath, said second emitter of green light being physically annexed to said probe housing;

the green light from said second emitter of green light having a second peak wavelength and a second wavelength band associated therewith;

said second peak wavelength being within the range of about 500–600 nm;

light at said second peak wavelength having absorption coefficients with respect to oxyhemoglobin and deoxyhemoglobin;

at least one of the absorption coefficients of light at said first peak wavelength being different than the respective absorption coefficient of light at said second peak wavelength;

the green light from said second emitter of green light interacting with deoxyhemoglobin in the volume of intravascular blood, thereby generating a second optical signal;

the second optical signal having an intensity; and (d) an electromagnetic radiation sensor, said electromagnetic radiation sensor adapted to be optically coupled to the skin surface for reception of the first and second optical signals, said electromagnetic radiation sensor being physically annexed to said probe housing.

20. A pulse oximeter probe according to claim 13 wherein said first peak wavelength is about 560 nm and said second peak wavelength is about 577 nm.

21. A pulse oximeter probe according to claim 14 wherein said first and second wavelength bands are less than or equal to 5 nm wide.

22. A pulse oximeter probe according to claim 14 wherein said first and second wavelength bands are about 1 nm wide.

23. A pulse oximeter probe according to claim 13 wherein said first and second peak wavelengths are within the range of about 540–577 nm.

24. A pulse oximeter probe according to claim 17 wherein said first and second wavelength bands are less than or equal to 5 nm wide.

25. A pulse oximeter probe according to claim 13 wherein said first and second emitters of green light each comprise a source of electromagnetic radiation and an optical bandpass filter.

26. A pulse oximeter probe according to claim 13 wherein said probe does not have any emitter of red or infrared light associated therewith.

27. A method of determining the oxygen saturation of hemoglobin at a central body site comprising the steps of:
   (a) illuminating skin at the central body site with electromagnetic radiation at a first green frequency to generate a first optical signal from the interaction between the electromagnetic radiation and blood under the skin at the central body site, the first optical signal having an intensity;
   (b) determining the intensity of the first optical signal;
   (c) illuminating the skin at the central body site with electromagnetic radiation at a second green frequency to generate a second optical signal from the interaction between the electromagnetic radiation and the blood under the skin at the central body site, the second optical signal having an intensity;
   (d) determining the intensity of the second optical signal; and
   (e) determining the oxygen saturation of hemoglobin using the intensity of the first optical signal and the intensity of the second optical signal.

28. A method of determining the oxygen saturation of hemoglobin at a central body site according to claim 27 wherein said step (e) comprises the step of determining the oxygen saturation of hemoglobin without using any parameter determined from interaction between the volume of intravascular blood and electromagnetic radiation within at least one of the red and infrared regions of the electromagnetic spectrum.

29. A method of determining the oxygen saturation of hemoglobin at a central body site according to claim 28 wherein said central body site comprises a wrist.

30. A method of determining the oxygen saturation of hemoglobin at a central body site according to claim 28 wherein said central body site comprises a thigh.

31. A method of determining the oxygen saturation of hemoglobin at a central body site according to claim 28 wherein said central body site comprises an abdomen.

32. A method of determining the oxygen saturation of hemoglobin at a central body site according to claim 28 wherein said central body site comprises a forehead.

33. A method of determining the oxygen saturation of hemoglobin at a central body site according to claim 28 wherein said central body site comprises a scalp.

34. A method of determining the oxygen saturation of hemoglobin at a central body site according to claim 28 wherein said central body site comprises a back.

35. A method of determining the oxygen saturation of hemoglobin at a central body site according to claim 27 wherein said central body site comprises a wrist.

36. A method of determining the oxygen saturation of hemoglobin at a central body site according to claim 27 wherein said central body site comprises a thigh.

37. A method of determining the oxygen saturation of hemoglobin at a central body site according to claim 27 wherein said central body site comprises an abdomen.

38. A method of determining the oxygen saturation of hemoglobin at a central body site according to claim 27 wherein said central body site comprises a forehead.

39. A method of determining the oxygen saturation of hemoglobin at a central body site according to claim 27 wherein said central body site comprises a scalp.

40. A method of determining the oxygen saturation of hemoglobin at a central body site according to claim 27 wherein said central body site comprises a back.

41. A method of determining the oxygen saturation of hemoglobin at a central body site according to claim 27 wherein said step (e) comprises the steps of:
   (a) collecting a first plurality of data values corresponding to a plurality of first optical signal intensities;
   (b) collecting a second plurality of data values corresponding to a plurality of second optical signal intensities; and
   (c) analyzing the first and second pluralities of data values in the frequency domain to determine the oxygen saturation of the hemoglobin.

* * * * *

UNITED STATES PATENT AND TRADEMARK OFFICE
Certificate

Patent No. 5,830,137                                      Patented: November 3, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: John Edward Scharf, Oldsmar, FL (US); and Stephan Peter Athan, Tampa, FL (US)

Signed and Sealed this Twenty-fourth Day of October 2006.

ALI IMAM
Supervisory Patent Examiner
Art Unit 3735